United States Patent [19]

Collins et al.

[11] 4,136,699

[45] Jan. 30, 1979

[54] ABSORBENT ARTICLE WITH ADHESIVE STRIP

[75] Inventors: James A. Collins, North Oaks; Thomas H. Quinn, St. Paul, both of Minn.

[73] Assignee: H. B. Fuller Company, St. Paul, Minn.

[21] Appl. No.: 760,831

[22] Filed: Jan. 21, 1977

Related U.S. Application Data

[63] Continuation-in-part of Ser. No. 590,936, Jun. 27, 1975, abandoned.

[51] Int. Cl.$^2$ .................. A61F 13/16; C08K 5/01; C09J 7/02
[52] U.S. Cl. .................. 128/290 R; 260/33.6 AQ; 260/876 B; 428/40; 428/355
[58] Field of Search .................. 428/40, 68, 74, 355; 128/290 R; 260/876 B, 33.6 AQ

[56] References Cited

U.S. PATENT DOCUMENTS

| 3,595,237 | 7/1971 | Sargent et al. | 128/290 R |
|---|---|---|---|
| 3,672,371 | 6/1972 | Roeder | 128/290 R |
| 3,686,107 | 8/1972 | Russell | 260/33.6 AQ |
| 3,862,068 | 1/1975 | Russell | 260/876 B |
| 3,897,783 | 8/1975 | Ginocchio | 128/290 R |
| 3,932,327 | 1/1976 | Naylor | 260/33.6 AQ |
| 3,935,338 | 1/1976 | Robertson | 428/40 |
| 3,954,692 | 5/1976 | Downey | 428/355 |
| 3,956,223 | 5/1976 | Chiang et al. | 260/876 B |
| 4,028,292 | 6/1977 | Korpman | 260/33.6 AQ |

*Primary Examiner*—William R. Dixon, Jr.
*Attorney, Agent, or Firm*—Merchant, Gould, Smith, Edell, Welter & Schmidt

[57] ABSTRACT

The disclosed article (e.g. a sanitary napkin) typically comprises (1) an elongated absorbent pad, (2) an outer covering layer in adherent contact with at least one surface of the pad, (3) an adhesive strip or layer on the exposed surface of the outer layer, and (4) a release liner for protecting the adhesive layer. The adhesive layer is useful for removably attaching the article to the inside of an undergarment or the like. Production of the article can be greatly simplified by using a hot-melt pressure sensitive adhesive (PSA) as the adhesive layer. However, the rubbery base for the hot-melt PSA should be very carefully selected. Two types of rubbery polymers provide good results, i.e. (a) an A-B-A block copolymer having polystyrene end blocks and a rubbery poly(ethylene-butylene) midblock and (b) a radial teleblock copolymer with branches having polystyrene terminal blocks and a butadiene segment in the center. One or both of these rubbery polymers is used to formulate the hot-melt PSA along with a suitable tackifier and a process oil.

7 Claims, No Drawings

ABSORBENT ARTICLE WITH ADHESIVE STRIP

CROSS REFERENCE TO RELATED APPLICATION

This application is a continuation-in-part of our copending application Ser. No. 590,936, filed June 27, 1975 now abandoned.

FIELD OF THE INVENTION

This invention relates to articles for absorbing fluids. An aspect of this invention relates to articles for absorbing body fluids such as blood, urine, menses, and other exudates, secretions, and excreta (including fecal matter). Still another aspect of this invention relates to a sanitary napkin provided with a pressure-sensitive adhesive means for attaching the napkin to a supporting garment.

DESCRIPTION OF THE PRIOR ART

Absorbent structures have been developed which are particularly well-suited for use with a supporting garment or body-encircling member, wherein the absorbent structure is temporarily attached to the member or garment with a pressure-sensitive adhesive means. Typical examples of such absorbent structures include sanitary napkins and diaper-like inserts for attachment to the inside of rubber panties. The inserts for rubber panties which serve, in combination with the panties, as diapers, are similar in structure to the sanitary napkins, except that they are wider and are designed to receive and absorb urine and fecal matter. The sanitary napkins are generally of two types—a highly absorbent type for periods of heavy menstrual flow and a far-less absorptive type for the so-called light flow (which typically occurs near the end of a menstrual period). An example of the highly absorbtive type of sanitary napkin is described in U.S. Pat. No. 3,672,371 (Roeder) issued June 27, 1972.

All of the aforementioned absorbent structures generally comprise (1) an elongated absorbent pad having essentially two major surfaces, (2) an outer covering layer adhered to one or both of the two major surfaces, (3) an adhesive layer on the outer layer which is intended for contact with the garment or body-encircling member, and (4) a release liner means for covering and protecting the adhesive layer until the absorbent structure is put to use.

Several types of pressure-sensitive adhesive systems have been suggested for use as the aforementioned pressure-sensitive adhesive layer on the outwardly-facing surface of the outer layer of the absorbent structure. For example, some work has been done with solvent-based pressure-sensitive adhesive (PSA) systems. However, the generally low-viscosity of such PSA systems can result in a rapid penetration or impregnation of the embodiment pad, leading to poorly controlled results with respect to coating of the PSA system. Furthermore, any solvent-based system can have the usual problems of health hazards from solvent vapors, solvent recovery to reduce costs, etc., associated with it.

Water-based adhesive systems have also been suggested for providing the PSA layer on the outer surface of the absorbent pad structure. It has been generally found, however, that the water-based adhesives tend to "set" or dry down rather slowly, particularly as compared to the solvent-based type.

Still another approach which has been attempted is the use of transfer tapes to transfer a coherent layer of PSA onto the desired portion of the pad structure. One difficulty with this approach is that the resulting coherent layer of adhesive can be used only as the PSA means for adhering the pad to the garment. Since there is no impregnation of the absorbant pad structure with the transferred adhesive, the adhesive does not ordinarily add to or reinforce the integrity of the absorbent pad structure. With a more fluid adhesive, it is at least possible to use the PSA system for a double purpose; as the PSA layer on the outer surface and as a means for cementing together seams (or the like) in the structure.

So-called hot-melt PSA's are known. However, these PSA systems typically lack one or more performance requirements for a sanitary napkin or a diaper pad PSA.

For example, the properties of hot-melt PSA's containing A-B-A block copolymers (particularly of the "KRATON" type) have been extensively studied, and these studies generally point to the conclusion that relatively large amounts of the copolymer (e.g. 25% or more, based on the weight of the adhesive) should be used for adequate adhesive properties. As a result, a "KRATON"-containing hot-melt pressure-sensitive adhesive is likely to have a high melt viscosity, e.g. in excess of 15,000 centipoise (cps) at 300° F. (about 150° C.). Melt viscosities can be reduced with plasticizing oils, as disclosed in U.S. Pat. No. 3,935,338 (Robertson et al), issued Jan. 27, 1976, but drastic losses of adhesive properties have been observed resulting from the addition of the oil, even when the amount of oil is smaller than the amount of "KRATON". ("KRATON" is a trademark of the Shell Oil Company.) Robertson et al have suggested the use of a "reinforcing resin" such as coumarone-indene in the PSA to improve adhesive properties without increasing melt viscosity. However, melt viscosities are still relatively high in such PSA's.

Still another problem with hot-melt PSA's based upon A-B-A block copolymers is likely to arise when careful control over the melt viscosity is needed. The A-B-A block copolymers which first became available typically contained polymerized butadiene or isoprene midblocks with at least some degree of remaining unsaturation or other structural characteristics which contribute to heat-instability. That is, structural changes, degradation, reaction with oxygen, or the like could occur in these heat-sensitive midblocks, resulting in significant viscosity changes in relatively short periods of time, e.g. time periods as short as a few hours. In those manufacturing processes where the viscosity of the hot-melt PSA did not need to be confined within rigid limits, these viscosity changes could oftentimes be tolerated. However, in other processes, a viscosity change of 30% or more in four hours or even as little as 10–20% in two hours could interfere with a well-controlled application of the adhesive.

A possible improvement in stability seemed to appear on the scene when relatively heat-stable A-B-A block copolymers became available. These newer copolymers (such as "KRATON" G) had polyolefin midblocks which behaved like saturated synthetic hydrocarbon rubbers and were far less sensitive to heat-induced changes in structure or physical properties. However, the uses of such relatively heat-stable copolymers appear to greatly aggravate the problem of reducing melt viscosity to a level suitable for commercially available hot-melt-applying machinery. For example, the following hot-melt pressure-sensitive adhesive formula has been disclosed in trade literature of the Shell Chemical Polymers Division of the Shell Oil Company:

| Parts by Weight | Ingredients |
|---|---|
| 100 | "KRATON G" (trademark of Shell Oil Company) |
| 150 | "WINGTACK 95" (trademark of Goodyear Tire and Rubber Company for synthetic terpene resin) |
| 50 | "PICCOTEX" (trademark for hydrocarbon resin) |
| 100 | "TUFFLO" (trademark for hydrocarbon process oil) |

According to this Shell Oil Company literature, the above-described hot-melt PSA was found to have a viscosity of 250,000 centipoise (cps) at 350° F. Although the reasons for such a high melt viscosity are not fully understood, it is presently believed that the partial incompatibility of the "WINGTACK 95" with "KRATON G" has a strong thickening effect.

Although wide ranges of plasticizing oil content and "KRATON" content are disclosed in the prior art, a satisfactory hot-melt PSA with a viscosity of 15,000 cps or less, a relatively small amount of "KRATON", a relatively large amount of plasticizing oil, good heat stability, and good cohesiveness is believed to be unavailable.

SUMMARY OF THE INVENTION

A hot-melt PSA system has now been discovered which can be used as the PSA for adhesive-coated absorbent structures. Such a hot-melt PSA system must meet a variety of exacting requirements including heat stability, relatively low viscosity ( 15,000 cps or less at 300° F.), adequate adhesive bond strength (shear resistance, peel resistance, etc.), adequate "quick stick" tack, resistance to cohesive failure, and the like. Furthermore, with respect to these properties, only relatively small deviations from a set norm can be tolerated. For example, excessive adhesive bond strength characteristics could be as deterimental to the ultimate product as excessive melt viscosity or melt viscosity changes would be in the manufacture of the article. Surprisingly, the heat-stable A-B-A block copolymers (such as "KRATON G") assist in controlling some or all of these desired properties, provided that sufficient tackifier and plasticizing oil are used. Like many hot-melt systems, the hot-melt PSA used in this invention comprises a tackifier, a rubbery-base material, and a plasticizer or diluent, e.g. a hydrocarbon process oil, for adjusting the tack, the viscosity, and the like. However, the amount of hydrocarbon process oil used in this invention is believed to be quite a typical and should be greater (by weight) than the A-B-A block copolymer. By properly selecting the amounts of hydrocarbon plasticizing oil and tackifier resin, a hot-melt pressure-sensitive adhesive is obtained which has excellent cohesive strength and virtually ideal "quickstick" tack and adhesive bond strength combined with a viscosity well suited to the available machines for applying adhesives to absorbent articles. In short, the result is considered to be a substantially ideal balance of properties for the uses and purposes disclosed in this application.

Two different types of heat-stable A-B-A block copolymers have been found to meet the requirements of a PSA for absorbent articles (e.g. sanitary napkins) and, further, to provide these surprising advantages. In one type (commercially available as "KRATON" G) the A blocks comprise polystyrene and the B block is a rubbery poly(ethylene-butylene) center block. The other type is a teleblock copolymer comprising molecules having at least three branches radially branching out from a central hub, each of the branches having polystyrene blocks and a butadiene segment in the center.

Thus, a typical absorbent structure of this invention comprises:
(a) an elongated absorbent pad having essentially two major surfaces;
(b) an outer layer in adherent contact with at least one of the two major surfaces;
(c) the hot-melt pressure-sensitive adhesive layer, which is adhered to the outwardly-facing surface of the outer layer, i.e. the surface which is designed to come in contact with the garment or body-encircling member; and
(d) a sheet-like removable protective release liner means covering the hot-melt pressure-sensitive adhesive layer.

DETAILED DESCRIPTION

As pointed out previously, a typical absorbent structure of this invention is a sanitary napkin of the type disclosed in U.S. Pat. No. 3,672,371 (Roeder), issued June 27, 1972. A structure of this general type can include an absorbent pad enclosed in a fluid-pervious wrapper which is overlapped to provide a seam, the seam typically running lengthwise through the middle of a major surface of the pad. The layer (or layers) of PSA (pressure-sensitive adhesive) can be applied to this seam (overlapped) area. If the PSA has sufficient fluidity when applied, it can permeate the seam, binding together the overlapped area and sealing the absorbent pad inside the fluid-pervious wrapper. A release liner over the PSA layer protects it until the napkin is to be used, at which time the liner is peeled off and the PSA layer is pressed against the inside of an underwear garment or the like. The major surface on which the PSA is coated does not actually have to be fluid-pervious, since the body fluids enter the absorbent structure from the opposite surface. For this reason, the absorbent structure can contain other elements such as a fluid-impervious film integral with the PSA-coated surface and the absorbent pad. Furthermore, the liner or envelope enclosing the absorbent pad can comprise a plurality of layers of material such as waterlaid sheets, nonwoven webs, and the like. The absorbent pad itself can be a batt or frictionally entangled mass of fibers with properties similar to an absorbent cotton mass. Absorbent cotton itself can also be used as the absorbent pad material.

When the purpose of the absorbent structure is to absorb a very light flow of blood and menses, the total structure can be simpler. In this case the absorbent pad can be much thinner and need not be surrounded or sealed in completely by a fluid-pervious layer, due to the inherently greater integrity of the thinner pad. For example, the entire structure can consist essentially of the thin pad (totally exposed on one major surface), a fluid-impervious film in adherent contact with the other major surface of the pad (this film serves as the outer covering layer), the PSA layer coated on the exposed surface of the impervious film, and the release liner protecting the PSA layer.

In any of these structures, the PSA layer need not be coextensive in area with the major surface on which it is coated. On the contrary, the typical PSA layer is very much narrower in width and can be somewhat shorter in length.

When the absorbent structure is an insert for rubber panties and is intended to serve as a diaper, it is typically wider than a sanitary napkin and may be somewhat longer. Otherwise, the structure is similar. On the other hand, if the absorbent structure is intended for receiving wound exudates, a different arrangement of elements is generally desirable.

The properties of the PSA layer are peculiar to this art. For example, the PSA, when applied, should have a low enough viscosity to flow into place readily and preferably also to permeate the aforementioned seam area or overlap area. However, the viscosity must not be so low that the PSA composition will permeate through the outer covering layer and into the absorbent pad itself. Furthermore, the viscosity should be high enough to permit some degree of a property similar to "hold-out" — that is, a significant amount of the PSA composition should remain on the exposed surface of the covering layer and form a coherent PSA layer. This "hold-out" effect can be most effectively obtained if the PSA, during application to the outer covering layer, has a significant amount of thixotropy. For a hot-melt PSA, it is ordinarily preferred that the composition have a viscosity ranging from about 500 to 15,000 centipoise (cps), preferably 500–10,000 cps, in the pour temperature range, which would typically be 100°–250° C., more typically 150°–200° C. (e.g. 300°–400° F.).

Another important property is the ability to solidify or congeal or "set" very rapidly — preferably almost instantaneously. Hot-melt PSA's are particularly desirable in this regard, since they can cool down from the application temperature to a solidification temperature almost instantly under normal ambient conditions.

Among the most peculiar properties needed for the PSA are the adhesive bond characteristics. These characteristics must be obtained without sacrificing room temperature tack ("quick stick" or "wet grab") and without creating a situation where the adhesive will offset or transfer to the garment. The requirements for the adhesive bond are that the PSA should have adequate peel strength and yet have the ability to release itself from the undergarment without pulling of fibers or tearing the garment. These are presently no adequate standardized tests for measuring these adhesive bond properties; however, the PSTC-1 test is helpful to give some indication of the required amount of peel strength. See U.S. Pat. No. 3,672,371, column 3, line 51 et seq. See also U.S. Pat. No. 3,954,692 (Downey), issued May 4, 1976, column 7, line 56 et seq. Standard shear tests are also helpful. For example, a PSA of the invention has been found to have a 180° peel strength ("Mylar" substrate, 12 in./min) ranging from about 4 to about 5 or 6 pounds per inch width (piw) and a tensile shear strength (0.1 in./min) of about 15 to about 35 pounds per square inch (psi).

The hot-melt PSA compositions which have been found to have the best combination of properties for use in sanitary napkins and diaper inserts comprise a relatively heat-stable rubbery or elastomeric block copolymer, an essentially hydrocarbon oil, and a tackifier resin, all of which are described in more detail subsequently.

THE RUBBERY COPOLYMER

The two basic types of heat-stable rubbery or elastomeric block copolymers particularly well-suited for use in this invention are:
(a) an A-B-A block copolymer having polystyrene end blocks and a rubbery polyolefin center or midblock, the polyolefin being a rubbery poly(ethylene-butylene) block, and
(b) a teleblock copolymer comprising molecules having at least three branches radially branching out from a central hub, each said branch having polystyrene terminal blocks and a butadiene segment in the center. It is believed that this type of block copolymer could also be described as having a branched polymerized butadiene mid-block with a polystyrene terminal block at the end of each branch.

The A-B-A block copolymer is considered a two-phase polymer comprising polystyrene domains in a rubbery poly(ethylenebutylene) matrix. In order to obtain desired levels of tack, it is tackified with a resin and an oil (and this is also true of the teleblock copolymer). The A-B-A polymer is a true elastomer (according to the ASTM definition of "elastomer") and has an elongation at break well in excess of 200%, e.g. 500%. The elongation at break for the teleblock (radial) copolymer is an approximately the same range or slightly higher, e.g. 590%.

To ensure rubberiness or elastomeric behavior in the radial copolymer, the number of butadiene units should be greater than the number of styrene units. Shore A hardness for the teleblock (radial) copolymers can be in the range typical of true rubbers, e.g. above 60 or 70.

The ultimate tensile strength of the rubbery copolymer (whether of the A-B-A type or the radial type) is moderately high, e.g. above 2,000 p.s.i., more typically above 3,000 p.s.i. Tensile strengths above 5,000 psi are possible with the A-B-A structure.

It has been found that the relative inertness and heat-stability of the ethyl-butylene midblock bears more similarly to polyolefins (such as polyethylene or polybutene) than to polymerized polyunsaturated compounds such as the low molecular weight dienes. Similarly, the branched polymerized butadiene midblocks exhibit relatively greater heat stability. This higher degree of heat stability carries over into hot-melt PSA formulas. Several other effects upon hot-melt PSA compositions are observed, some of which would be expected to be beneficial and others not so beneficial. Surprisingly, it has been found that, for the field of use contemplated for hot-melt PSA's of this invention, all or virtually all of the effects of using 10–20% by weight of the relatively heat-stable block copolymer along with 120–400 parts by weight of plasticizing oil (per 100 parts of block copolymer) are beneficial, assuming a suitable amount of a partially incompatible tackifier resin is included in the PSA composition.

It is known that certain inherent advantages can flow from the use of an A-B-A block copolymer with a polyolefin (i.e. poly-mono-olefin) midblock as compared to a generally straight-chain poly-di-olefin midblock such as polyisoprene or polybutadiene. Although this invention is not bound by any theory, the higher degree of unsaturation in straight-chain poly(akladienes) is believed to contribute to heat-instability. A branched chain poly(alkadiene) wherein the branches are tipped with polystyrene has some of the advantages of a polyolefin midblock, however. With respect to the polystyrene-polymonoolefin-polystyrene structure, e.g. "KRATON G" rubbers, data available from Shell Oil Company indicate that the ultimate tensile strength and modulus at 300% extension are considerably higher for "KRATON" G as opposed to "KRATON" 1107 or 1102. Elongation at break is less for "KRATON" G and, perhaps most important, solution viscosity has been found to be considerably higher for the G-type "KRATON", i.e. the A-B-A block copolymer with the poly-mono-olefin midblock. According to Shell literature, the solution viscosity of "KRATON" G in 25 weight percent solution in toluene is 12,000 cps (Brookfield Model RVT viscometer). Furthermore, "KRATON G" has less compatibility with the standard terpene tackifier resins as compared to the A-B-A block copolymers with midblocks made from low molecular weight alkadienes.

The difficulties which might be expected to result from the thickening effect of the poly-mono-olefin midblock is not encountered in the context of this invention. Although this invention is not bound by any theory, it is believed that potentially excessive viscosities are avoided because of the combination of partial incompatibility with the tackifier and the surprisingly high cohesive strength of a hot-melt PSA containing the polystyrene-poly(ethylene-butylene)-polystyrene structure. The unusually high cohesive strength permits the use of atypically large amounts of plasticizing oil, resulting in an adhesive with good "quickstick" tack; good adhesive bond strength, when the PSA is in the solid state; and very manageable viscosity, when the PSA is in the molten state. In other words, the drastic loss of PSA properties reported by Robertson et al. in U.S. Pat. No. 3,935,338, observed with block copolymer amounts in excess of 25% by weight of the PSA composition and plasticizing oil amounts considerably less than 100 parts per hundred (based on the weight of the block copolymer) create no potential source of difficulty in the context of the present invention. As will be explained subsequently, proportions of block copolymer, plasticizing oil, and tackifier used in this invention improve "quickstick" tack and other desired properties without increasing the risk of the cohesive failure of the adhesive. As a given viscosity, a hot-melt PSA based on a suitable heat-stable A-B-A block copolymer with a poly-mono-olefin midblock can have a significantly higher ultimate tensile strength and also a higher modulus at 300% elongation. For example, by using "KRATON" G, a PSA can be formulated to have a low viscosity at the application temperature (extremely important in most sanitary pad applications) and still have a high cohesive strength, thereby minimizing adhesive transfer from the pad to an undergarment or the like. Furthermore, a problem generally associated with low-viscosity PSA's, i.e. rapid penetration or impregnation of the absorbent pad, is not observed with hot-melt PSA's of this invention. And all these desired advantages are obtained along with a greater heat stability, e.g. in the 300°–400° F. temperature range, so that the viscosity of the molten PSA in the hot-melt reservoir remains relatively constant and controllable for hours at a time. A less heat-stable A-B-A block copolymer in the PSA could lead to viscosity changes as high as 40% in eight hours.

THE ESSENTIALLY HYDROCARBON OIL

The oily liquids used in compounding PSA's of this invention are essentially hydrocarbon process oils which are preferably low in aromatic content. For example, an analysis of the types of carbon atoms in oils used in this invention indicate that aromatic carbons comprise less than 5% of the oil, while naphthenic carbons (i.e. carbons of cycloaliphatic compounds and the like) can range from about 25 to 60% and paraffinic carbons can range from about 35 to 75%. Accordingly, these oils are typically referred to as "naphthenic" or "paraffinic" process oils.

These oils are preferably very low in volatility. Initial boiling points, under normal ambient pressure conditions, can range from well over 400° F. (i.e. above about 200° C.) to almost 800° F. (almost 430° C.). The least volatile fraction in the process oils can have a boiling point in excess of about 1000° F. (about 535° C.), so that the entire boiling range can cover several hundred degrees, e.g. 600°–1100° F. (315°–600° C.).

The aromatic content of the oils as determined by clay gel analysis (in weight percent) can range from less than 1% up to 15% or more; however, aromatic content should be low and should not exceed about 20% by weight. The molecular weight of the oil is typically above 200 and can be above 600. Most naphthenic and paraffinic process oils, however, tend to have a molecular weight within the range of 250–600.

THE TACKIFIER RESIN

Although various types of tackifier resins are known, such as hydrogenated rosin esters, esters of polyhydric alcohols, phenol-aldehyde resins, and the like, the preferred tackifiers are of the type known as "hydrocarbon resins". In industrial practice "hydrocarbon resin" is a term of art relating to resins in the molecular weight range of a few hundred up to about 6,000 or 8,000 which are obtained or synthesized from rather basic hydrocarbonaceous materials such as petroleum, coal tar, turpentine, and the like. A good description of "hydrocarbon resins" can be found in Kirk-Othmer, Encyclopedia of Chemical Technology, Second Edition, Volume 11, Interscience, New York, 1966, pp 242. Many of the so-called "hydrocarbon resins" commercially available today are "terpene" resins, i.e. polymers with repeating isoprene ($C_5H_8$) or $C_{10}H_{16}$ units. These polymers can be natural or synthetic and can be copolymers (including terpolymers, etc.), since isoprene is an olefin which can be copolymerized with other olefins. Terpene-phenols are also produced.

All hydrocarbon resins do not work with equal effectiveness in this invention. It is preferred that the hydrocarbon resin (i.e. tackifier resin) component consist essentially of natural or synthetic polymers which are partially incompatible with the preferred A-B-A block copolymers. Such partial incompatibility is observed with a synthetic terpene resin having a softening point (ball and ring method) of about 80° to about 115° C., particularly the commercially available resin known as "WINGTACK" 95, which is more compatible with "KRATON" 1101, 1102, or 1107 than with "KRATON G". "WINGTACK" 95 has a softening point (ball and ring method) of 100° C. plus or minus 5° C. and is believed to be a by-product of isoprene or polyisoprene production. It is also believed to be derived from a mixed olefin feedstock. According to U.S. Pat. No. 3,935,338 and South African Patent No. 700,881, "WINGTACK" 95 (trademark of Goodyear Tire and Rubber Company) is a thermoplastic tackifying resin essentially comprising a copolymer of piperylene and 2-methyl-2-butene which results from the cationic polymerization of 60% piperylene, 10% isoprene, 5% cyclopentadiene, 15% 2-methyl-butene, and about 10% dimer. Other tackifying resins of the same general type typically comprise 20-80 weight percent of piperylene and 80-20 weight percent of 2-methyl-butene. "WING-TACK 95" is preferred over natural terpenes and even over other synthetic terpenes. For reasons which cannot presently be explained, other tackifying resins (particularly those of the rosin ester type) can have an undesirable effect upon PSA properties. Thus, although mixtures of tackifying resins may be permitted in the context of this invention, the use of a "reinforcing resin" (as in U.S. Pat. No. 3,935,338) is not contemplated.

The naturally occurring terpenes can be classified as monocyclic (dipentene), dicyclic (pinene), or acyclic (mycrene) and may contain benzenoid groups. The synthetic terpene resins described in column 3, line 36 through column 4, line 9 of U.S. Pat. No. 3,935,338 can be considered to be "cyclic", due to the presence of a small amount of cyclopentadiene. The major portion of the tackifying resin molecule, however, contains open chains derived from isoprene, piperylene (i.e. 1,3-pentadiene), and the like.

Other Ingredients

As is known in the art, various other components can be added to modify the tack, rheology characteristics (including melt viscosity, thixotropy, and the like), adhesive bond strength characteristics, rate of "set", low temperature flexibility, etc., color, odor, etc., of a hot-melt PSA. For example, liquid resins are sometimes used as a partial or total replacement or substitution for process oils, although such a substitution is not preferred in the context of this invention.

It is generally preferred that the other components or ingredients should be relatively inert and should have negligible effects upon the properties contributed by the tackifier resin, the block copolymer, and the plasticizing or process oil. Thus, ingredients such as waxes which might unduly reduce tack should be used, if at all, in very minor amounts. Pigments or pigment dispersions would ordinarily be the most commonly used additional ingredients. As is shown in the art, antioxidants and other stabilizing ingredients can be added to hot-melt PSA's to protect against degradation, but such additives do not appear to be essential in compositions of this invention.

The Resulting Hot-Melt PSA Compositions

The hot-melt PSA compositions of this invention can be formulated with techniques known in the art using heated mixers and the like. The rubbery copolymer and the oil can be blended together readily at moderately elevated temperatures (e.g. 150°-300° F.). The tackifier resin can be added to the copolymer-oil mixture. If a pigment is included in the PSA composition, it should be added to the copolymer/oil blend before the tackifier resin is introduced into the composition.

The resulting hot-melt PSA, once it is heated to the temperature where it will flow readily, can be applied to the outer covering layer of the absorbent structure or article by any of the techniques known in the art, including flow coating, roller coating, knife coating, or the like. The PSA can also be extruded into place by using a hot-melt extruder or die face.

As noted previously, hot-melt PSA's of this invention can have a viscosity within the range of 500-15,000 centipoise, measured at 300°-400° F. (e.g. 300° F. or 150° C.) using a Brookfield Thermosel, spindle SC-4-37, 20 rpm. Viscosities less than 10,000 cps are preferred.

The "quick stick" and adhesive bond strength properties of PSA's of this invention should be carefully selected for use in sanitary pads. Furthermore, these properties must be balanced against adequate cohesive strength. In addition to the inconvenience and possible damage to undergarments caused by adhesive transfer, there is also the danger that the peel strength will be too high, resulting in damage to the undergarment when a used sanitary pad is to be removed and discarded. Furthermore, the adhesive bond must be resistant to attack by bodily fluids such as urine, menses, and the like.

It presently appears that the PSTC-1 test can give some indication of the degree of peel strength which should be provided by the bond between the PSA coating and the undergarment. For example, a PSTC-1 180° peel value of less than about 3 pounds per inch width (p.i.w.) would probably provide inadequate adherence of the pad to the undergarment in most cases, even though the actual bond strength under conditions of use would not be predictable in advance and is probably not measurable by any known test. PSTC-1 values in excess of 4 p.i.w. would be typical in commercial embodiments of PSA's made according to this invention. When "quick stick" tack is determined by the loop tack test, wherein an adhesive coated, "MYLAR" (trademark for poly(ethylene terephthalate), made by the duPont Company) is touched to a glass plate, the force necessary to pull it apart with a tensile tester (such as an "Instron") is measured in pounds per inch width (p.i.w.). The "quick stick" or "quick tack" measurements obtained by this test are numerically somewhat similar to a 180° peel test, since a somewhat similar type of force is applied to the adhesive bond, albeit for a different purpose. Preferred PSA's of this invention have a "quick stick" (by the loop method) which is greater than 3 p.i.w. and normally greater than 5 p.i.w. Measurements approaching 13 p.i.w. can be readily obtained in practice, but a "quick stick" within the range of about 6-12 p.i.w. is ordinarily very adequate for sanitary or absorbent pad use. Similarly, PSTC-1 values in excess of 13 or 14 p.i.w. are unnecessary and possibly even undesirable, due to the risk of tearing or otherwise damaging the undergarment or fabric substrate.

Hot-melt PSA's of this invention made with polystyrene-poly(ethylene-butylene)-polystyrene (even amounts of this A-B-A copolymer well below 20% by weight) tend to be moderately hard materials in the solid state at 23° C., as indicated by penetrometer tests, wherein a 200 gram weight drives a needle into the sample for a five-second time period. The distance that the needle sinks is the "penetration", which is measured in millimeters. Penetrometer values less than 200 mm are obtained in practice.

Softening points (determined by the ring and ball method) for PSA's of this invention normally exceed about 85° C. (185° F.), e.g. 90° C. or higher. The drop melt point (also determined by the ring and ball method) can be several degrees higher than the sag point (the point at which the PSA begins to soften). In short, softening ranges are typically above 200° F. but below 300° F. (above about 90° C. and below about 150° C.).

PSA's of this invention exhibit relatively low "set". The "set" is determined by measuring the difference between the original length of a sample ($L_1$) and the length of the same sample after it has been elongated 500% and allowed to resume essentially its original configuration. The length of the relaxed sample (L$_2$) minus L$_1$ is then expressed as a percentage of "set". Only a PSA with significant cohesive strength and/or significant elastomeric behavior will have a measurable "set". If the composition is too soft to have significant cohesive strength or elastomeric behavior, it will do a very poor job of returning to its original configuration — e.g., it could retain as much as 100% or more of the elongation, or it could fail or break during the elongation step of the test. Hot-melt PSA's used in this invention should have sufficient cohesive strength to have a measurable "set". Similarly, these PSA's should have a measurable tensile strength at 500% elongation, i.e. a measurable 500% modulus.

With respect to penetration, softening point, 500% modulus, percent set, and other physical properties, presently available data indicate that neither polystyrene-polyisoprene-polystyrene nor polystyrene-polybutadiene-polystyrene can be substituted for the preferred A-B-A block copolymers used in this invention.

For example, it has been found that a polystyrene-polyisoprene-polystyrene polymer ("KRATON" 1107) cannot apparently be used to make a PSA containing more than 100 parts per hundred by weight of plasticizing or process oil (based on the weight of the "KRATON"), if cohesive strength of the PSA is to be preserved and adhesive transfer to the undergarment is to be avoided. Although there may be techniques of formulation which would permit the use of significant quantities of oil in combination with "KRATON" 1107 in a PSA without drastic loss of cohesive strength, such techniques are believed to be outside the scope and criteria of the present invention, wherein the PSA preferably consists essentially of a three-component system (block copolymer/oil/tackifier), and any additional components are preferably present in very minor amounts.

PROPORTIONS OF COMPONENTS OF THE PSA

The proportions of components in a hot-melt PSA of this invention are selected to provide the PSA characteristics described previously. It is also important that these adhesive characteristics remain reasonably constant during storage or non-use in a hot-melt applicator and during normal storage of the article (e.g. a sanitary napkin) prior to use. Still further, it is desirable that adhesive properties remain generally within the prescribed ranges from one production batch to another. "Aging" tests of the polystyrene-poly(ethylene-butylene)-polystyrene embodiment of the PSA indicate generally stable adhesive properties at hot-melt applicator temperatures (e.g. with the range of 100°–250° C., more typically 150°–200° C.) and, after coating onto the article, with the range of temperatures typically associated with storage and shipping (e.g. from about −20° C. to about +50° C.).

With respect to this embodiment, the most noticeable downward trend in adhesive properties detectable upon storage of coated samples in 1 to 24-week aging tests appears to be in the peel strength of samples stored at 120° F. (48.9° C.). Even this trend does not indicate a significant deterioration in peel strength.

In short, these data generally indicate a reasonable degree of stability in the internal structure of the hot-melt PSA. For example, the process oil is reasonably well retained within a matrix or the like provided by the tackifier resin and/or the rubbery block copolymer.

The tackifier resin (e.g. "WINGTACK" 95, trademark of Goodyear Chemical Company), provides a number of desired properties (e.g. increased shear strength of the adhesive bond) particularly at levels in excess of 30 weight-% (e.g. 40 weight-% or more). However, if the resin is increased at the expense of the process oil content, there can be a significant loss of tack and undesirable increases in viscosity. Accordingly, the amounts of tackifier resin is preferably less than 65 weight-%.

The process oil content is preferably above 15% by weight to provide sufficient tack and a low enough viscosity at the pour temperature or temperature of application (e.g. 150°–200° C.). However, excessive amounts of oil (for a given content of rubbery base) can reduce shear strength and cohesive strength, as is known in the art. What may be less well known is the ability of the process oil to continue to boost "quick stick" tack as the amount of oil in the PSA is increased beyond 100 parts per hundred (phr), based on the weight of the block copolymer, and, surprisingly, throughout the range of about 120 to about 350 phr. When the oil content is in the range of 350–450 phr, the decrease in "quick stick" tack has been found to be startling. It is very difficult to obtain adequate "quick stick" tack with an oil content above 400 phr, though the "quick stick" in the 350–400 phr range is at least marginally acceptable, and is generally excellent in the 150–300 phr range.

The rubbery copolymer base assists in providing many, if not most, of the key properties contemplated for hot-melt PSA's of this invention, and particularly sanitary pads of this invention, provided the PSA contains about 40–65% by weight tackifier resin and 120–400 phr oil. Thus, minor amounts of these rubbery materials are effective. Excessive amounts can increase the viscosity drastically, interfering with flow properties in the 100°–250° C. range discussed previously.

The following Table sets forth broad, preferred, and optimum amounts of the various components of PSA's of this invention. Desired viscosities are also set forth in the Table. Although viscosity adjustments can be made by adding volatile solvents (i.e. solvents with an initial boiling point below 200° C. at normal atmospheric pressure), it is preferred that PSA compositions of this invention be essentially 100% "solids" (essentially free of volatiles).

|  | Broad | Preferred | Optimum |
|---|---|---|---|
| Block Copolymer | wt %: 10–20<br>phr: — (wt) | 10–20<br>— | 13–16.5<br>— |
| Terpene | wt %: 40–65<br>phr: 250–500 | 40–60<br>300–400 | 50–60<br>300–400 |
| Oil | wt %: 15–40<br>phr: 120–400 | 25–40<br>150–350 | 25–35<br>150–300 |
| Inert Additives | wt %: <25<br>phr: 0–100 | <5<br><10 | <5<br><10 |
| Brookfield Viscosity | <15,000 cps at 300° to 400° F. | 500–10,000 cps at 300° F. | 500–8,000 cps at 300° F. |

In the case of the oil content, it is particularly important that both the percentage and phr limits be observed.

The principle and practice of this invention is illustrated in the following non-limiting Examples.

EXAMPLE 1

In this Example, a block copolymer with the A-B-A structure was used. The commercial embodiment of the copolymer is sold by Shell Chemical Company under the trademark "KRATON" GX 6500 (more recently referred to as "KRATON" 1650). This commercially available material is a three block copolymer with polystyrene endblocks and a rubbery poly(ethylene-butylene) midblock. It is considered a two-phase polymer consisting of polystyrene domains in a rubbery poly(ethylene-butylene)matrix. Typical properties of the copolymer are as follows:

Tensile strength psi: 6000
Elongation at break: 500%
Modulus at 300% extension, psi: 950
Solution viscosity (measured with a Brookfield Model RVT Viscometer):
20% by weight in toluene, centipoise: 2000
25% by weight in toluene, centipoise: 12000

The product is available in particulate form, e.g. in crumbs about one-eighth inch in size.

The formula for the hot-melt PSA of this Example, was as follows:

| Parts by Weight | Ingredient |
| --- | --- |
| 30.0 | Naphthenic process oil* |
| 15.0 | "KRATON" 1650 (trademark; formerly sold under the trademark "KRATON" GX 6500) |
| 1.0 | Pigment dispersion (43 parts by weight of pigment dispersed in 57 parts by weight of the naphthenic process oil) |
| 54.0 | "Wingtack" 95 (trademark of Goodyear Chemical Co. for hydrocarbon tackifier resin) |

*See detailed description which follows.

After the "KRATON" was completely blended into the process oil, the pigment dispersion was added under high shear mixing. The mixing temperature was maintained below 300° F. After the pigment was dispersed in the "KRATON"/oil composition, the "Wing-tack" 95 was added, and mixing was continued until a uniform composition was obtained.

The naphthenic process oil used in the composition was "Tufflo 6204" (trademark). This process oil has a viscosity (SUS/100° F.) of 1965, a specific gravity (60/60) of 9.9206, a flash point (COC) of 440° F., a pour point of 0° F., and a sulfur content which is less than 0.001%. The molecular weight of the oil is 440, and clay gel analysis indicates 0% asphaltenes, 9% polar compounds, or resins, 14.8% aromatics, and 85.2% saturates. Carbon type analysis indicates 2% aromatic carbons, 52% naphthenic carbons, and 46% paraffinic carbons. The boiling range is 630°–1018° F., the initial boiling point being 630° F., and 95% of the oil being distilled at 1018° F. Only 5% of the oil distills at 630° F. and 50% distills at 710° F.

Ten pounds of the resulting hot-melt PSA was tested for peel strength and shear strength. The 180° peel strength was conducted at 12 inches per minute and the tensile shear test was conducted at 0.1 inches per minute. Results were as follows:

| Aging Time* | Peel (piw) | Shear (psi) |
| --- | --- | --- |
| Zero | 4.9 | 29.1 |
| 8 hours | 5.2 | 30.7 |
| 24 hours | 4.6 | 29.8 |
| 48 hours | 4.8 | 32.3 |

*Length of time adhesive was held in the hot-melt applicator pot at 193° C. (380° F.) prior to application to the test specimens.

Three samples were tested and averaged to arrive at the values given in the above table.

Properties of the resulting hot-melt PSA were as follows:

Ring and ball softening point: 202°–240° F.
Specific gravity: 0.922
Brookfield Viscosity (Brookfield Thermosel speed 20 rpm spindle SC-4-27, 8 gram sample):
1,300–1,650 cps at 350° F.
3,800–5,000 cps at 325° F.
700–900 cps at 375° F.

This hot-melt PSA was found to be particularly well-suited for sanitary napkin structures of the type described in U.S. Pat. No. 3,672,371.

EXAMPLE 2

This Example illustrates the use of a radial (teleblock) copolymer, the commercial embodiment in this case being "SOLPRENE" 502, a trademark of Philips Petroleum Company; typical properties of "SOLPRENE" (trademark) 502-CX are as follows:

Specific gravity: 0.91
Melt flow, 190° C./21.6 Kg: 0.2
Molecular weight: 91000
Shore A hardness: 79
Butadiene/styrene ratio: 70/30
Tensile strength, psi: 3900
Modulus at 300% extension, psi: 540
Elgonation at break: 590%
Compression set (Method B) 22 hours, 78° F.: 35%

The formula used in the case of the "SOLPRENE" polymer was as follows:

| Parts by Weight | Ingredient |
| --- | --- |
| 29.0 | Naphthenic process oil ("TUFFLO" 6204, see Example 1) |
| 15.0 | "SOLPRENE" 502 (see preceding description) |
| 2.0 | Pigment dispersion (see Example 1) |
| 54.0 | "WINGTACK" 95 (trademark; see Example 1) |

The procedure for preparing the hot-melt PSA was the same as that of Example 1. The specific gravity of the resulting product was 0.922. The ring and ball softening point was 204°–240° F., the viscosity at 350° F. was 750–940 centipoise (cps), determined on a Brookfield Thermosel at a speed of 20 rpm, spindle SC-4-27, with an 8 gram sample.

EXAMPLE 3

The purpose of this Example was to illustrate the effect of substituting polystyrene-polydiolefin-polystyrene for "KRATON" GX 6500 in the formulation of Example 1. The A-B-A copolymer with the polydiolefin midblock selected for the comparison was "KRATON" 1107 (trademark of Shell Oil Company). The composition made from "KRATON" 1107 is hereinafter referred to as the "Polydiolefin Control".

The following properties were measured: penetration (using an Instrument-Lab line penetrometer); ring and ball softening range (sag point to drop-melt point); viscosity (Brookfield Thermosel, model RVT); 180° peel according to PSTC-1; 500% modulus; and % "set"; all of these tests having been described previously. The results are set forth in Table I.

TABLE I
COMPARISON OF EXAMPLE 1 COMPOSITION AND POLYDIOLEFIN MIDBLOCK CONTROL

| Test | Example 1 | Polydiolefin Control |
|---|---|---|
| Penetration (mm/5 sec.) | 90.6 | 240.2 |
| Softening Point, ° F., (sag - drop melt) | 203–238 | 156–188 |
| Viscosity, cps | 1750 | 285 |
| PSTC-1, peel (p.i.w.) | 8.3 (40 g/m² coat wt.) | 2 (54 g/m² coat wt.) |
| 500% modulus, psi | 12.9 | too soft to measure |
| % set | 21.8 | too soft to measure |

A study of viscosity changes vs. elapsed time was made, using the Brookfield Thermosel, model RVT. The results are set forth in Table II.

TABLE II
VISCOSITY vs. TIME AT 400° F.

| Hours Elapsed | Example 1 | | Polydiolefin Control | |
|---|---|---|---|---|
| 1 - initial | 525 | | 135 | |
| 2 | 500 | | 115 | |
| 3 | 480 | | 100 | |
| 4 | 470 | Total Change 17% | 90 | Total Change 55% |
| 5 | 460 | | 80 | |
| 6 | 455 | | 75 | |
| 7 | 445 | | 70 | |
| 8 | 440 | | 65 | |
| 9 | 435 | | 60 | |

EXAMPLE 4

The purpose of this Example was to investigate the effect of various oil/"KRATON" ratios on the "quick stick" tack of compositions of Example 3.

The Example 1 composition and the "Polydiolefin Control" were tested, as in Example 3, but these compositions were modified as follows:

| Composition | Description |
|---|---|
| 4-1-0 | Example 1 formula with oil ("TUFFLO") omitted (0% by weight oil). |
| 4-C-0 | "Polydiolefin Control" with oil omitted (0% by weight oil). |
| 4-1-150 | Example 1 formula, with 150 phr by wt. of oil, based on the weight of "KRATON". |
| 4-C-150 | "Control" formula, with 150 phr oil, same basis. |
| 4-1-300 | Example 1 with 300 phr oil, same basis. |
| 4-C-300 | "Control" with 300 phr oil, same basis. |
| 4-1-450 | Example 1 with 450 phr oil, same basis. |
| 4-C-450 | "Control" with 450 phr oil, same basis |

The "quick stick" tack test was the loop tack test described previously. Cohesive failure, if observed during the test, was noted.

| Composition | Cohesive Failure? | "Quick Stick" (in lb/in width) |
|---|---|---|
| 4-1-0 | No | 0.67 |
| 4-C-0 | No | 0.0 |
| 4-1-150 | No | 12.75 |
| 4-C-150 | Yes | 10.1 |
| 4-1-300 | No | 6.1 |
| 4-C-300 | Yes | 5.5 |
| 4-1-450 | No | 1.7 |
| 4-C-450 | Yes | 3.1 |

What is claimed is:

1. In an article for absorbing fluids, the structure comprising:
  (a) an elongated absorbent pad having essentially two major surfaces;
  (b) an outer layer in adherent contact with at least one of said two major surfaces;
  (c) a hot-melt pressure sensitive adhesive layer adhered to the outwardly facing surface of said outer layer, said hot-melt pressure-sensitive adhesive having a viscosity of 500 to 15,000 centipoise at its pour temperature, said pour temperature ranging from about 300° to about 400° F., said hot-melt pressure-sensitive adhesive comprising:
    (i) 10–20% by weight of a rubbery copolymer selected from the group consisting of a radial block-copolymer, an A-B-A block copolymer, and mixtures thereof, said radial block copolymer being a teleblock copolymer comprising molecules having at least three polymerized butadiene branches radially branching out from a central hub, each said branch having polystyrene terminal blocks; said A-B-A block copolymer having polystyrene end blocks and a rubbery, essentially saturated, poly(mono-olefin)-like midblock,
    (ii) more than 120 but less than 500 parts by weight, per 100 parts by weight of said rubbery copolymer of an essentially hydrocarbon oil selected from the group consisting of naphthenic oils, paraffinic oils, and mixtures thereof; the amount of said oil in said hot-melt pressure-sensitive adhesive composition being within the range of 15 to 40% by weight;
    (iii) more than 250 but less than 500 parts per 100 parts by weight of said rubbery copolymer, of terpene tackifier resin; the amount of terpene tackifier resin in said composition being within the range of 40 to 60% by weight.

2. An article according to claim 1 wherein said structure of said article further comprises a sheet-like, removeable protective release liner means covering said hot-melt pressure-sensitive adhesive layer.

3. An article according to claim 1 wherein said structure is a sanitary napkin, and wherein said outer layer means is a fluid-pervious non-woven wrapper comprising a substantially rectangular sheet enveloping said absorbent pad.

4. An article according to claim 3 wherein said hot-melt pressure-sensitive adhesive layer comprises an elongated strip of said adhesive, narrower in width than the width of said absorbent pad, which has at least partially impregnated said nonwoven wrapper along a seam of said wrapper, thereby holding said wrapper in adherent contact with said major surface of said absorbent pad.

5. A hot-melt pressure-sensitive adhesive composition having a Brookfield viscosity ranging from about 500 to 15,000 centipoise at the pour temperature, said pour temperature ranging from about 300° to about 400° F., said composition being substantially free of solvents with a boiling point below 200° C. at atmospheric pressure and consisting essentially of:
  (a) 10–20% by weight of a rubbery A-B-A block copolymer having polystyrene end blocks and a rubbery, essentially saturated, poly(mono-olefin)-like midblock, said A-B-A block copolymer being at least partially incompatible with terpene tackifying resins, said A-B-A block copolymer having a modulus at 300% extension of at least about 500 p.s.i. and an ultimate tensile strength in excess of about 2,000 p.s.i.;

(b) from about 300 to about 400 parts by weight, per 100 parts by weight of said A-B-A block copolymer, of terpene tackifier resin; the amount of said terpene tackifier resin in said composition ranging from 40 to 60% by weight;

(c) from about 150 to about 350 parts by weight of an essentially hydrocarbon oil selected from the group consisting of naphthenic oils, paraffinic oils, and mixtures thereof; the amount of said essentially hydrocarbon oil in said composition ranging from 15 to 40% by weight;

said pressure-sensitive adhesive composition having a measurable 500% modulus at 23° C., being resistant to cohesive failure in P.S.T.C.−1 180° peel strength tests throughout the aforementioned range of essentially hydrocarbon oil content, and exhibiting P.S.T.C.−1 values in excess of about 4 pounds per inch width.

6. A pressure-sensitive adhesive composition according to claim 5, wherein:

said pressure-sensitive adhesive is a 100% solids composition having a Brookfield viscosity of 500–10,000 centipoise at 300° F.; and said pressure-sensitive adhesive consists essentially of said A-B-A block copolymer, wherein said midblock is poly(ethylene-butylene); said terpene tackifier resin; said essentially hydrocarbon oil; and 0–100 parts by weight, per 100 parts by weight of said A-B-A block copolymer, of essentially inert extenders, fillers, pigments, or colorants.

7. In combination with a sanitary napkin comprising an elongated absorbent pad having essentially two major surfaces and an outer envelope means comprising a fluid-pervious nonwoven sheet-like wrapper encircling said absorbent pad having a seam therein running lengthwise along a said major surface, the improvement which comprises:

a hot-melt pressure-sensitive adhesive layer impregnated into said seam and thereby adhered to the outwardly facing surface of said wrapper, said hot-melt pressure-sensitive adhesive being the hot-melt pressure-sensitive adhesive composition of claim 5.

* * * * *

UNITED STATES PATENT AND TRADEMARK OFFICE
CERTIFICATE OF CORRECTION

PATENT NO. : 4,136,699
DATED : January 30, 1979
INVENTOR(S) : James A. Collins and Thomas H. Quinn It is certified that error appears in the above-identified patent and that said Letters Patent are hereby corrected as shown below:

```
Column 1, line 58, for "embodiment" read --absorbent--.
Column 3, line 51, for "a typical" read --atypical--.
Column 6, line 21, for ethylenebutylene" read
   --ethylene-butylene--.
Column 6, line 42, for "similarly" read --similarity--.
Column 7, line 45, for "As" read --At--.
Column 9, line 43, for "shown" read --known--.
Column 10, line 1, for "SC-4-37" read --SC-4-27--.
Column 13, line 41, for "Wing-tack" read --Wingtack--.
Column 14, lines 14, 15, 16, for
   "Brookfield Viscosity (Brookfield Thermosel speed 20
 rpm
      spindle SC-4-27, 8 gram sample):"
   read
   "Brookfield Viscosity (Brookfield Thermosel speed 20
 rpm spindle SC-4-27, 8 gram sample):--.
```

Signed and Sealed this

Twentieth Day of November 1979

[SEAL]

Attest:

RUTH C. MASON
Attesting Officer

LUTRELLE F. PARKER
Acting Commissioner of Patents and Trademarks